United States Patent [19]

Redmond et al.

[11] Patent Number: 5,245,987
[45] Date of Patent: Sep. 21, 1993

[54] SURGICAL INSTRUMENT WITH EXTENDABLE BLADES

[75] Inventors: Russell J. Redmond, Goleta; Claude A. Vidal, Santa Barbara, both of Calif.

[73] Assignee: VIR Engineering, Santa Barbara, Calif.

[21] Appl. No.: 923,338

[22] Filed: Jul. 31, 1992

[51] Int. Cl.⁵ .............................................. A61B 17/02
[52] U.S. Cl. ...................................... 128/20; 606/198
[58] Field of Search ................. 128/20, 749, 757, 759; 606/191, 198; 604/104–109, 265

[56] References Cited

U.S. PATENT DOCUMENTS

| | | | |
|---|---|---|---|
| 1,972,428 | 9/1934 | Richard | 604/105 |
| 3,961,620 | 6/1976 | Schack et al. | 128/757 |
| 5,092,345 | 3/1992 | Sakita | 128/757 |
| 5,152,279 | 10/1992 | Wilk | 128/20 |

FOREIGN PATENT DOCUMENTS

| | | | |
|---|---|---|---|
| 2528273 | 10/1976 | Fed. Rep. of Germany | 604/265 |
| 0629823 | 10/1978 | U.S.S.R. | 128/20 |

Primary Examiner—Max Hindenburg
Attorney, Agent, or Firm—James E. Brunton

[57] ABSTRACT

A tissue retraction device for use in laparoscopic surgery which includes a plurality of thin, resiliently deformable, pre-stressed blades disposed in a stacked relationship within an outer sleeve. The blades are connected at their inboard ends to a support rod which is telescopically carried within the sleeve. The blades are pre-twisted about a stratigically located pivot point so that once the inboard end of the device is positioned within the peritoneum, the rod can be urged forwardly causing the end portions of the blades to automatically fan out in a manner such that the full width of the blades can be pressed against the tissue.

15 Claims, 1 Drawing Sheet

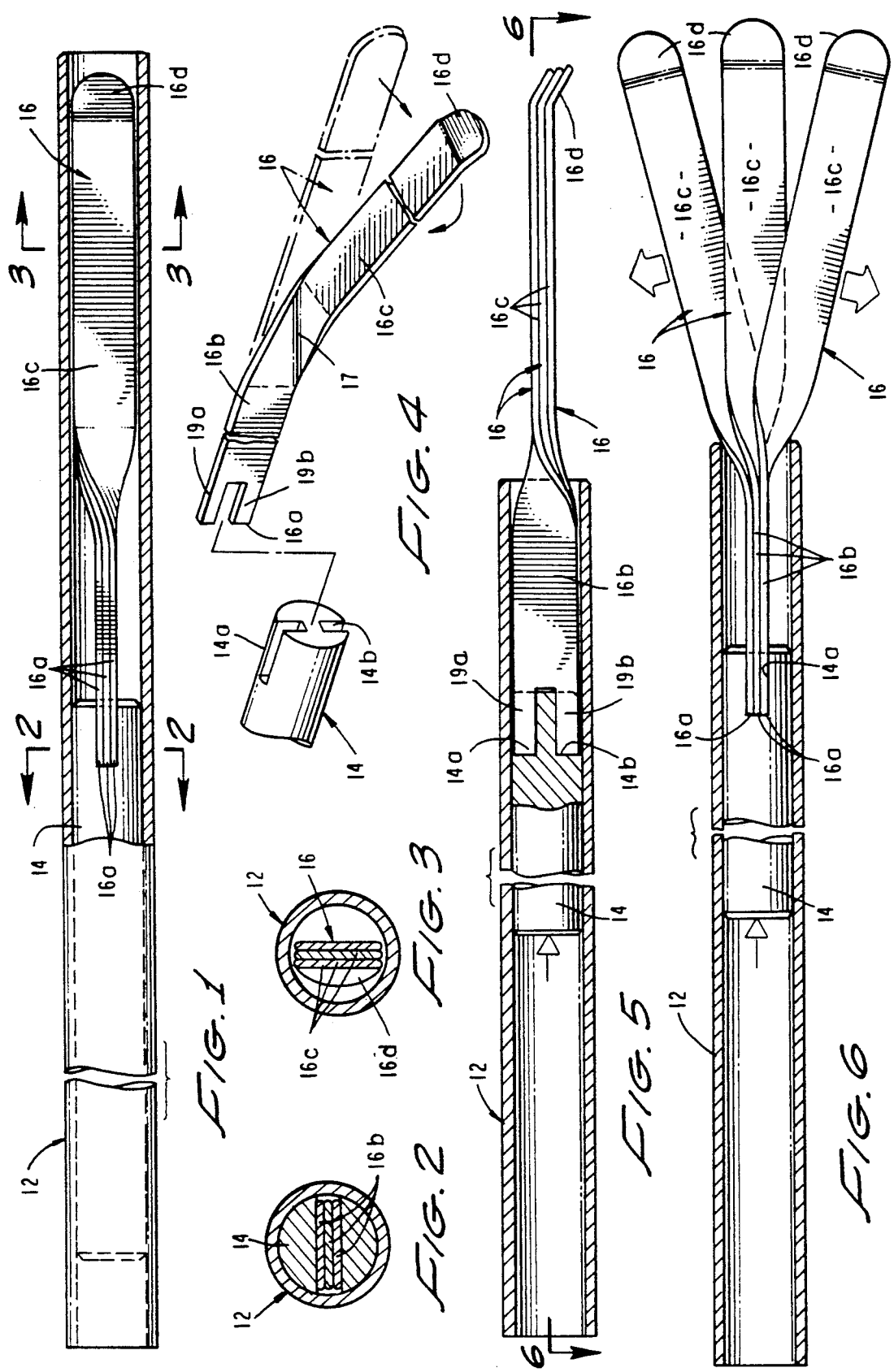

SURGICAL INSTRUMENT WITH EXTENDABLE BLADES

BACKGROUND OF THE INVENTION

1. Field of the Invention

The present invention relates generally to surgical instruments. More particularly, the invention concerns tissue retraction device that will fit within a small diameter trocar and will open or "fan out" once within the peritoneum.

2. Discussion of the Invention

During the performance of laparoscopic surgery, the surgeon will have occasion to retract tissue and other structures from the abdominal cavity. In the past, this has typically been accomplished using graspers and retractors of various sizes and designs. As a general rule, these prior art devices are relatively large and cumbersome to work with and, on occasion, can cause serious injury to the patient.

The apparatus of the present invention, provides for the first time, a very small, easy to use instrument which will conveniently fit within a trocar as small as five millimeters in diameter. The device can include one or more specially configured blades which can be extended outwardly once the blade is in position within the peritoneum.

In one form of the invention, a plurality of thin, resiliently deformable, pre-stressed blades are provided in a stacked relationship within an outer sleeve and are connected at their inboard ends to a support rod telescopically carried within the sleeve. The blades are pre-twisted about a stratigically located pivot point so that once the inboard end of the device is positioned within the peritoneum, the rod can be urged forwardly causing the end portions of the blades to automatically fan out in a manner such that the full width of the blades can be pressed against the tissue. By retracting the rod, the blades can be pulled into the sleeve and returned to their stacked and aligned configuration within the outer sleeve.

SUMMARY OF THE INVENTION

It is an object of the present invention to provide a surgical instrument which is very small but sturdy and easy to use for the retraction of tissue and the like during laparoscopic surgery.

More particularly, it is an object of the invention to provide a device of the aforementioned character which will conveniently fit within a five millimeter tracor.

Another object of the invention is to provide an instrument as described in the preceding paragraph which includes a plurality of very thin tissue engaging blades, which are stacked together during insertion of the instrument into, for example, the peritoneum, but can be caused to automatically fan out within the peritoneum so that the full width of the blades can be used for tissue manipulation.

Another object of the invention is to provide an instrument of the character described in which one or several blades can be used and in which the blades can be specially configured and formed from a wide variety of materials so that the device can be precisely tailored for a number of end uses.

Still another object of the invention is to provide an instrument as described in the preceding paragraphs which embodies a minimum number of moving parts, is easy for the surgeon to use and can be inexpensively manufactured.

BRIEF DESCRIPTION OF THE DRAWINGS

FIG. 1 is a foreshortened, top plan view, partly in cross-section to show internal construction, of one form of the surgical instrument of the present invention.

FIG. 2 is a cross-sectional view taken along lines 2—2 of FIG. 1.

FIG. 3 is a cross-sectional view taken along lines 3—3 of FIG. 1.

FIG. 4 is a generally perspective, fragmentary, exploded view of the elongated rod portion and one blade of the apparatus.

FIG. 5 is a foreshortened, side-elevational view of the apparatus partly in cross-section to show internal construction.

FIG. 6 is a view taken along lines 6—6 of FIG. 5.

DESCRIPTION OF ONE FORM OF THE INVENTION

Referring to the drawings and particularly to FIGS. 1, 4, and 5, the surgical instrument of the present invention can be seen to comprise an elongated, generally cylindrically-shaped sleeve 12 and an elongated, cylindrically-shaped rod 14 which can be telescopically received within sleeve 12 for sliding movement from the retracted position shown in FIG. 1 to the extended position shown in FIG. 6. As best seen in FIG. 6, the apparatus of this form of the invention also includes a plurality of thin, yieldably deformable blades 16 which are connected to rod 14 proximate their inboard ends 16a.

Referring also to FIGS. 2 and 3, it is to be noted that when the rod 14 is in the retracted position, blades 16 reside within the sleeve in a stacked relationship with the planar surfaces of the blades being in close proximity with one another. It is also to be noted that each of the blades 16 has a longitudinal axis which is coaxially aligned with the longitudinal axis of sleeve 14.

As illustrated in FIG. 4, each of the blades 16 is twisted out of plane along a diagonally extending line 17, which is located at the junction of first and second portions 16b and 16c of the blade. Each of the blades is constructed of a resiliently deformable material such as spring steel or plastic so that, after portion 16c is twisted relative to portion 16b, it will tend to return to its original non-twisted configuration. Stated another way, when the blades are twisted about the longitudinal axis of the blades and along junction line 17, internal stresses will be imparted to the blades tending to continuously urge the second portion of the blades toward their original non-twisted configuration relationship. As a result of these internal stresses, when the rod 14 is moved into its second or extended position as shown in FIG. 6, the blades will tend to automatically fan out with respect to one another in the manner shown in FIG. 6, with the second portion of each of the blades coming to rest in a plane that extends at an obtuse angle with respect to the plane of the first portion of the blade.

When rod 14 is returned to its retracted position, the blades will enter the open end of sleeve 12 and will once again be urged into the stacked and aligned relationship shown in FIG. 1. Advantageously, the twisted portions of the blades provide camming surfaces to assist in smoothly urging the blades into their stacked orientation as they are drawn back into the sleeve. More particularly, as noted in FIGS. 2 and 3, when the blades are in the stowed position within sleeve 12, the first portion 16b of each blade resides in a plane which is generally perpendicular to the plane of each of the blade portions 16c. Because the width of the blades closely correspond to the diameter of the sleeve, the blades will be held in this stacked configuration so long as they are retained within sleeve 12. However, once rod 14 is pushed forwardly, as illustrated in FIG. 6, the memory retained by the second portion of each of the blades 16 will cause the blades to attempt to return to their original non-twisted configuration and, as a result, the blades will fan out or spread apart in the finger-like manner illustrated in FIG. 6. In this position, the full width of the blades have substantial strength due to the intermediated, twisted portion of each blade and, therefore; can advantageously be pressed against the tissue.

Referring once again to FIG. 4, it is to be noted that support 14 is provided with a pair of diametrically opposed slots 14a and 14b. Similarly, each of the blades 16 is provided with a pair of spaced-apart ears 19a and 19b which are closely receivable within slots 14a and 14b of rod 14. With this construction, each of the blades is securely anchored at its inboard end to rod 14 so that portion 16b of each blade is restrained against movement about its longitudinal axis. However, such anchoring of the blades does not impede the tendency of the second portions 16c of the blades to out of the plane and into the configuration shown in FIG. 6.

In the form of the invention shown in the drawings, each of the blades is provided with an outboard tip portion 16d which is disposed in a plane that extends at an angle with respect to the plane of portion 16c of the blade. Tip portions 16d are useful in the manipulation of tissue during the surgical procedure.

While blades 16 can be constructed of various materials and have various sizes, the instrument of the present invention is ideally suited for use in connection with a laparoscopic surgery. Therefore, the blades 16 are very small and preferably are of a size that can be received within a 5 millimeter trocar. For certain end applications, blades 16 can be coated with a lubricating material, or a protective coating, or they can otherwise be specially treated. By way of example, each blade could be provided with a dacron, reinforced silicon sheeting which is vulcanized around the blade. Such blades would provide a soft, non-sticking surface which would facilitate the manipulation of tissue during the surgical procedure.

As appropriate, the sleeve, the blades and the elongated rod 12, can be constructed of metal, plastic or other suitable material. When the components are constructed of a plastic material, the apparatus can be manufactured so inexpensively that disposal of the instrument after each use is economically warranted.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A surgical instrument for use in connection with the performance of laparoscopic procedures, comprising:

(a) an elongated, generally cylindrically shaped sleeve;
   (b) an elongated rod telescopically receivable within said sleeve for sliding movement therewithin from a retracted position to an extended position; and
   (c) a plurality of yieldably deformable blades connected to said rod and extending therefrom, said blades being receivable within said sleeve in a stacked, substantially aligned configuration, each said blade having a first and second portion, said second portion of each said blade having a longitudinal axis, said second portion being twisted relative to said first portion at a location proximate the junction of said first and second portions to urge said blades to fan outward with respect to one another whereby when said elongated rod is in said extended position said blades move out of alignment and into a fan shaped configuration with said longitudinal axes of said second portions of said blades extending angularly with respect to one another.

2. An instrument as defined in claim 1 in which each said blade is twisted so that when said elongated rod is in said retracted position, said second portion of each said blade is disposed in a plane extending generally perpendicular to the plane of said first portion.

3. An instrument as defined in claim 2 in which when said elongated rod is in said extended position, said second portion of each said blade is disposed in a plane extending at an obtuse angle with respect to the plane of said first portion of said blade.

4. An instrument as defined in claim 3 in which each said blade is constructed of spring steel and in which said second portion of each said blade terminates in a segment disposed within a plane that extends at an angle with respect to the plane of said second portion of said blade, said segments being arcuately spaced apart when said blades fan out.

5. An instrument as defined in claim 4 in which each said elongated rod is provided with a pair of slots and in which said blade includes a pair of ears closely receivable within said slots.

6. An instrument as defined in claim 5 in which the diameter of said elongated sleeve is less than about five millimeters.

7. An instrument as defined in claim 6 in which each said blade is covered with silicone sheeting.

8. A surgical instrument for use in connection with the performance of laparoscopic procedures, comprising:

(a) an elongated, generally cylindrically shaped sleeve;
   (b) an elongated rod telescopically receivable within said sleeve for movement therewithin from a retracted position to an extended position; and
   (c) at least three yieldably deformable blades connected to said rod and extending therefrom, said blades being receivable within said sleeve in a stacked, substantially aligned configuration, each said blade having a first and second portion, said second portion of each said blade having a tip portion and being twisted relative to said first portion at a location proximate the junction of said first and second portions to urge said second portion out of plane with said first portion and to impart internal stresses to said blade tending to continuously urge said second portions of said blades to fan apart when said elongated rod is in said extended position so that said tip portions are angularly spaced apart.

9. An instrument as defined in claim 8 in which when said elongated rod is in said extended position, said second portion of each said blade is disposed in a plane extending at an obtuse angle with respect to the plane of said first portion of said blade.

10. An instrument as defined in claim 9 in which the diameter of said elongated sleeve is less than about 5 millimeters.

11. A surgical instrument for use in connection with the performance of surgical procedures, comprising:
   (a) an elongated, generally cylindrically shaped sleeve;
   (b) at least two yieldably deformable blades receivable within said sleeve in a stacked, substantially aligned configuration, each said blade having a first portion and a second portion having a longitudinal axis and a tip, said second portion of each said blade being twisted relative to said first portion at a location proximate the junction of said first and second portions to impart internal stresses to said blade tending to continuously urge said blades to fan outwardly with respect to one another; when said second portions of said blade are in said extended position said longitudinal axes of said second portions of said blades extend angularly with respect to one another and said tips are spaced apart.
   (c) means for extending said second portions of said blades from said sleeve whereby when said second portions of said blades are in said extended position said longitudinal axes of said second portions of said blades extend angularly with respect to one another and said tips are spaced apart.

12. An instrument as defined in claim 11 in which said elongated rod is provided with a pair of slots and in which said blade includes a pair of ears closely receivable within said slots.

13. An instrument as defined in claim 11 in which when said elongated rod is in said extended position, said second portion of said blade is disposed in a plane extending at an obtuse angle with respect to the plane of said first portion of said blade.

14. An instrument as defined in claim 13 in which said blades are constructed of metal and in which said tips of said second portions of said blades extend angularly downwardly.

15. A surgical instrument for use in connection with the performance of laparoscopic procedures, comprising:
   (a) an elongated, generally cylindrically shaped sleeve;
   (b) an elongated rod telescopically receivable within said sleeve for sliding movement therewithin from a retracted position to an extended position; and
   (c) first and second yieldably deformable, generally planar blades connected to said rod and extending therefrom, each of said blades having curved tip portions and spaced apart, generally parallel edges, said blades being receivable within said sleeve in a stacked, configuration with said edges of said first blade being substantially aligned with said edges of said second blade, each said blade having a longitudinal axis and a first and second portion, said first portions being disposed in first planes and said second portions being twisted about said longitudinal axis at a location proximate the junction of said first and second portions to urge said second portions into second planes generally perpendicular to said first plane, whereby internal stresses are imparted to said blades tending to cause said second portions of said blades to fan outwardly with respect to one another so that said edges of said second portion of said first blade extend angularly with respect to said edges of said second portion of said second blade and said tip portions of said second portions of said first and second blades are angularly spaced apart.

* * * * *